United States Patent
O'Neill et al.

(10) Patent No.: US 10,285,608 B2
(45) Date of Patent: May 14, 2019

(54) MAGNETIC RESONANCE SAFE CABLE FOR BIOPOTENTIAL MEASUREMENTS

(71) Applicant: KONINKLIJKE PHILIPS N.V., Eindhoven (NL)

(72) Inventors: Francis Patrick O'Neill, Kissimmee, FL (US); Eduardo Mario Rey, Orlando, FL (US); Mark Deems Nelson, Satellite Beach, FL (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 567 days.

(21) Appl. No.: 14/400,085

(22) PCT Filed: May 27, 2013

(86) PCT No.: PCT/IB2013/054353
§ 371 (c)(1),
(2) Date: Nov. 10, 2014

(87) PCT Pub. No.: WO2013/175457
PCT Pub. Date: Nov. 28, 2013

(65) Prior Publication Data
US 2015/0141792 A1    May 21, 2015

Related U.S. Application Data

(60) Provisional application No. 61/651,844, filed on May 25, 2012, provisional application No. 61/739,753, filed on Dec. 20, 2012.

(51) Int. Cl.
*A61B 5/0408*  (2006.01)
*A61B 5/0428*  (2006.01)
(Continued)

(52) U.S. Cl.
CPC ...... *A61B 5/04087* (2013.01); *A61B 5/04286* (2013.01); *A61B 5/055* (2013.01);
(Continued)

(58) Field of Classification Search
CPC . A61B 5/0033; A61B 5/04087; A61B 5/0486; A61B 5/055; A61B 5/6832;
(Continued)

(56) References Cited

U.S. PATENT DOCUMENTS

| | | | |
|---|---|---|---|
| 6,032,063 A | 2/2000 | Hoar et al. | |
| 7,039,470 B1 * | 5/2006 | Wessman | A61N 1/05 607/122 |

(Continued)

FOREIGN PATENT DOCUMENTS

| | | |
|---|---|---|
| JP | 4071536 A | 3/1992 |
| JP | 5023399 | 2/1993 |

(Continued)

OTHER PUBLICATIONS

Van Genderingen, H. R., et al.; Carbon-fiber electrodes and leads for electrocariography during MR imaging; 1989; Radiology; 17(3)872.
(Continued)

*Primary Examiner* — Eun Hwa Kim

(57) ABSTRACT

A cable for use in biopotential measurements in a magnetic resonance (MR) environment comprises a flexible plastic or polymer sheet (32, 40) extending as a single unitary structure from a first end to an opposite second end, and an electrically conductive trace (38, 58) disposed on the flexible plastic or polymer sheet and running from the first end to the opposite second end. The electrically conductive trace has sheet resistance of one ohm/square or higher, and may have a hatching or checkerboard pattern. The cable may further include an electrically insulating protective layer (50, 70) disposed on the substrate and covering the electrically (Continued)

Figure 2:
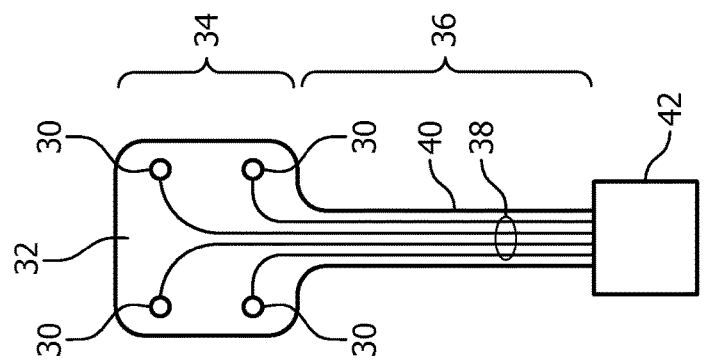

conductive trace, an electrode (30) disposed on the electrically conductive trace at the second end, an edge connector (74) at the first end, or various combinations of such features.

16 Claims, 6 Drawing Sheets

(51) Int. Cl.
    *A61B 5/055*     (2006.01)
    *A61B 5/00*     (2006.01)
    *H01B 1/02*     (2006.01)
    *H01B 3/30*     (2006.01)
    *H01B 7/17*     (2006.01)

(52) U.S. Cl.
    CPC ............. *A61B 5/6832* (2013.01); *H01B 1/02* (2013.01); *H01B 3/30* (2013.01); *H01B 7/17* (2013.01); *A61B 2562/0215* (2017.08); *A61B 2562/0217* (2017.08)

(58) Field of Classification Search
    CPC .......... A61B 2562/22; A61B 2562/221; A61B 2562/222; H01B 7/17; H01B 1/02222
    USPC ........ 600/386, 372, 373, 381, 393, 395, 396
    See application file for complete search history.

(56) References Cited

U.S. PATENT DOCUMENTS

| | | | |
|---|---|---|---|
| 7,272,427 B2 | 9/2007 | Ristolainen | |
| 8,480,577 B2 | 7/2013 | Tuccillo | |
| 2002/0168290 A1* | 11/2002 | Yuzhakov | A61B 5/14514 422/400 |
| 2004/0094324 A1* | 5/2004 | Barr | H01B 7/0009 174/117 F |
| 2004/0225210 A1* | 11/2004 | Brosovich | A61B 5/0428 600/372 |
| 2006/0085049 A1* | 4/2006 | Cory | A61B 5/0536 607/48 |
| 2006/0247509 A1* | 11/2006 | Tuccillo | A61B 5/04286 600/372 |
| 2010/0016702 A1 | 1/2010 | Greene | |
| 2011/0025429 A1* | 2/2011 | Syal | H01P 3/081 333/34 |
| 2011/0237921 A1* | 9/2011 | Askin, III | A61B 5/0408 600/377 |
| 2011/0301665 A1* | 12/2011 | Mercanzini | A61N 1/0531 607/45 |
| 2011/0306860 A1 | 12/2011 | Halperin et al. | |

FOREIGN PATENT DOCUMENTS

| | | |
|---|---|---|
| JP | 6261882 | 9/1994 |
| JP | 9276240 | 10/1997 |
| WO | 2006116677 A2 | 11/2006 |
| WO | 2006121469 A1 | 11/2006 |
| WO | 2011/056967 | 5/2011 |

OTHER PUBLICATIONS

Pickard, R. S., et al.; Flexible printed-circuit probe for electrophysiology; 1979; Medical and Biological Engineering and Computing; 17(2)261-267.

* cited by examiner

MAGNETIC RESONANCE SAFE CABLE FOR BIOPOTENTIAL MEASUREMENTS

CROSS REFERENCE TO RELATED APPLICATIONS

This application is a national filing of PCT application Ser. No. PCT/IB2013/054353, filed May 27, 2013, published as WO 2013/175457 A1 on Nov. 28, 2013, which claims the benefit of U.S. provisional application Ser. No. 61/651,844 filed May 25, 2012 and U.S. provisional application Ser. No. 61/739,753 filed Dec. 20, 2012, both of which are incorporated herein by reference.

The following relates to the sensor arts, measurement arts, magnetic resonance arts, safety arts, biopotential measurement arts including electrocardiography (ECG), electromyography (EMG), electroencephalography (EEG) electroretinography (ERG), and so forth, gated MR imaging arts employing cardiac gating or the like, and so forth.

In conventional biopotential measurements such as electrocardiograph (ECG), electroencephalograph (EEG), and similar measurements, electrical potentials are measured by electrodes placed on the skin. Conventionally, cabling with high electrical conductivity, e.g. using copper wires, is employed to connect the electrodes with the monitoring electronics.

When biopotential measurements are performed while the subject is disposed in a magnetic resonance (MR) scanner, the conventional high conductivity cabling is replaced by high resistance cabling. This is in deference to numerous problems that can arise in placing high conductivity cabling in the MR environment, including problems such as heating caused by RF pulses and/or magnetic field gradients, radio frequency interference issues, and so forth. Use of ECG or other biopotential measurement instruments in an MR setting has numerous applications. For example, ECG signals can be used to monitor the condition of the patient, and/or can be used to trigger or gate certain events such as imaging data acquisition. Cardiac gating performed in this way can reduce motion artifacts due to the beating heart.

In the MR room due to the RF heating effects and burn hazards associated with the MRI environment, a distributed or discrete high-resistance cable is used to connect the electrode to the MRI patient monitor with ECG functionality. These high resistance cables are expensive and can still be susceptible to heating and consequent risk of burns to the patient. They are cumbersome to manufacture, can suffer from inductive pickup, are susceptible to triboelectric effects, can suffer from parasitic capacitance, and are sensitive to patient movement. Routing of discrete lead wires can lead to inconsistency and inaccuracies in ECG performance.

Radio frequency (RF) fields produced by the MR scanner can generate currents in the cable, or "hot-spots" that may increase surface temperatures enough to exceed those allowed by regulatory standards and pose discomfort or a burn hazard to the patient. MR magnetic field gradients can cause interference and can also induce currents on the ECG cables and connections points, producing an additive interference waveform components that potentially give false heart rate readings, obscure ECG R-wave detection schemes, or otherwise degrade the ECG analysis. Cables employing a plated snap connector at each electrode location also introduce a time-consuming manual task of connecting each disposable electrode to a re-usable cable consisting of discrete wires and connectors.

Tuccillo et al., U.S. Pub. No. 2006/0247509 A1 discloses an a cable for use in an MRI, which is adapted to resist motion in response to magnetic fields generated by the MR scanner. The cable of Tuccillo et al. is constructed of a flexible Kapton substrate on which a plurality of conductive traces are drawn using a conductive carbon ink. In the disclosed embodiment, the carbon ink has a resistance of 10 ohm/sq while the cable is six feet in length and has a distributed impedance of about 330 ohms/cm. The ends of the cable include expanded regions with copper pads for connection to an ECG electrode at one end and an ECG monitor at the opposite end.

Electrodes for biopotential measurements also pose difficulties in an MR environment. A known electrode is a silver-silver chloride (Ag—AgCl) electrode. This type of electrode is also used in the construction of MR-compatible ECG electrodes in efforts to reduce DC offset voltage created by the half-cell potential of the electrode and to minimize contact impedance. Either a paste or gel is used as the electrolyte interface to the patient. Van Genderingen et al., "Carbon-Fiber Electrodes and Leads for Electrocardiography during MR Imaging", Radiology vol. 171 no. 3 page 872 (1989) discloses replacing conventional Ag—AgCl ECG electrodes with braided metal leads with ECG electrodes made of carbon fiber with plastic reinforced carbon fiber leads (Carbo Cone RE-I, Sundstroem, Sweden). They report that the carbon fiber electrodes did not degrade the images as compared with the conventional Ag—AgCl electrode/braided metal leads, and the plastic reinforcement made the carbon fiber leads less susceptible to bending as compared with similar leads made of graphite.

The following contemplates improved apparatuses and methods that overcome the aforementioned limitations and others.

According to one aspect, a cable for use in biopotential measurements in a magnetic resonance (MR) environment is disclosed. The cable comprises: a flexible plastic or polymer sheet extending as a single unitary structure from a first end to an opposite second end; an electrically conductive trace disposed on the flexible plastic or polymer sheet and running from the first end to the opposite second end, the electrically conductive trace having sheet resistance of one ohm/square or higher; and an electrode disposed on the electrically conductive trace at the second end. The electrode includes: a layer of electrically conductive material disposed on the electrically conductive trace at the second end that is more electrically conductive than the material comprising the electrically conductive trace; and an attachment layer disposed on the layer of electrically conductive material and configured to attach the electrode to human skin.

According to another aspect, a cable for use in biopotential measurements in a magnetic resonance (MR) environment is disclosed. The cable comprises: a flexible plastic or polymer sheet extending as a single unitary structure from a first end to an opposite second end; an electrically conductive trace disposed on the flexible plastic or polymer sheet and running from the first end to the opposite second end, the electrically conductive trace having sheet resistance of one ohm/square or higher; an electrically insulating protective layer disposed on the substrate and covering the electrically conductive trace; and an edge connector at the first end comprising a layer or layer stack of electrically conductive material disposed on the electrically conductive trace at the first end that is more electrically conductive than the material comprising the electrically conductive trace, the electrically insulating protective layer not covering the layer or layer stack of electrically conductive material.

According to another aspect, a cable for use in biopotential measurements in a magnetic resonance (MR) environment is disclosed. The cable comprises: a flexible plastic or polymer sheet extending as a single unitary structure from a first end to an opposite second end; and an electrically conductive trace disposed on the flexible plastic or polymer sheet and running from the first end to the opposite second end, the electrically conductive trace having sheet resistance of one ohm/square or higher, the electrically conductive trace having a hatching or checkerboard pattern.

According to another aspect, a biopotential measurement apparatus comprises: an electrode configured for attachment to skin of a human or animal; a monitor or receiver unit configured to receive biopotential measurements; and a cable as set forth in any of the three immediately preceding paragraphs connecting the electrode with the monitor or receiver unit.

One advantage resides in providing a magnetic resonance-compatible cable for ECG or other biopotential measurements with reduced susceptibility to eddy currents.

Another advantage resides in providing a magnetic resonance-compatible cable for ECG or other biopotential measurements that is robust against interference.

Another advantage resides in providing a magnetic resonance-compatible cable for ECG or other biopotential measurements that simplifies acquisition setup.

Numerous additional advantages and benefits will become apparent to those of ordinary skill in the art upon reading the following detailed description.

The invention may take form in various components and arrangements of components, and in various process operations and arrangements of process operations. The drawings are only for the purpose of illustrating preferred embodiments and are not to be construed as limiting the invention.

Figure 1:
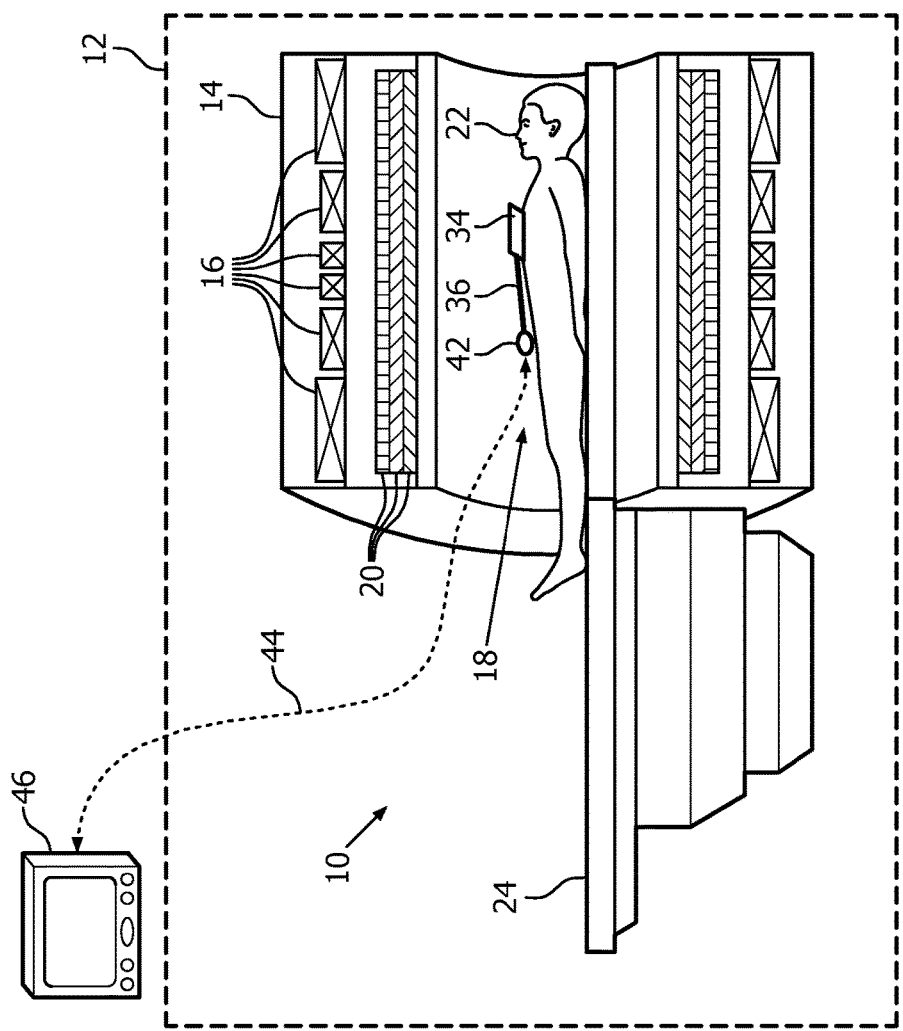

FIG. 1 diagrammatically shows a magnetic resonance (MR) system with an electrocardiograph (ECG) operating inside the MR scanner.

FIG. 2 diagrammatically shows the ECG acquisition system.

Figure 3:
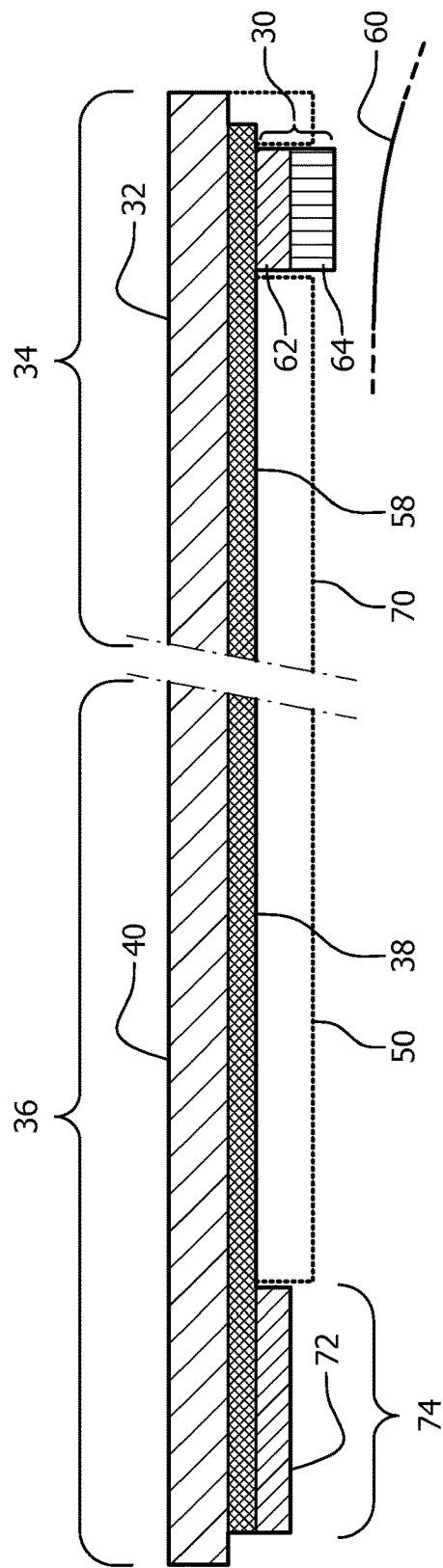

FIG. 3 diagrammatically shows an electrode and proximate portion of cable as disclosed herein.

Figure 4:
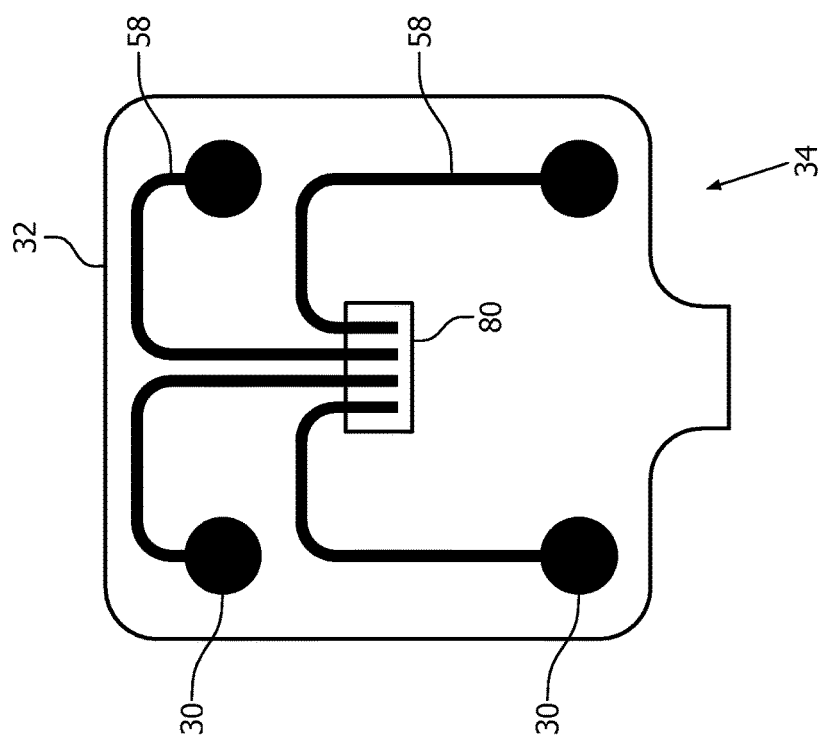

FIG. 4 diagrammatically shows an electrode patch with uniformly distributed high resistance printed circuitry.

Figure 5:
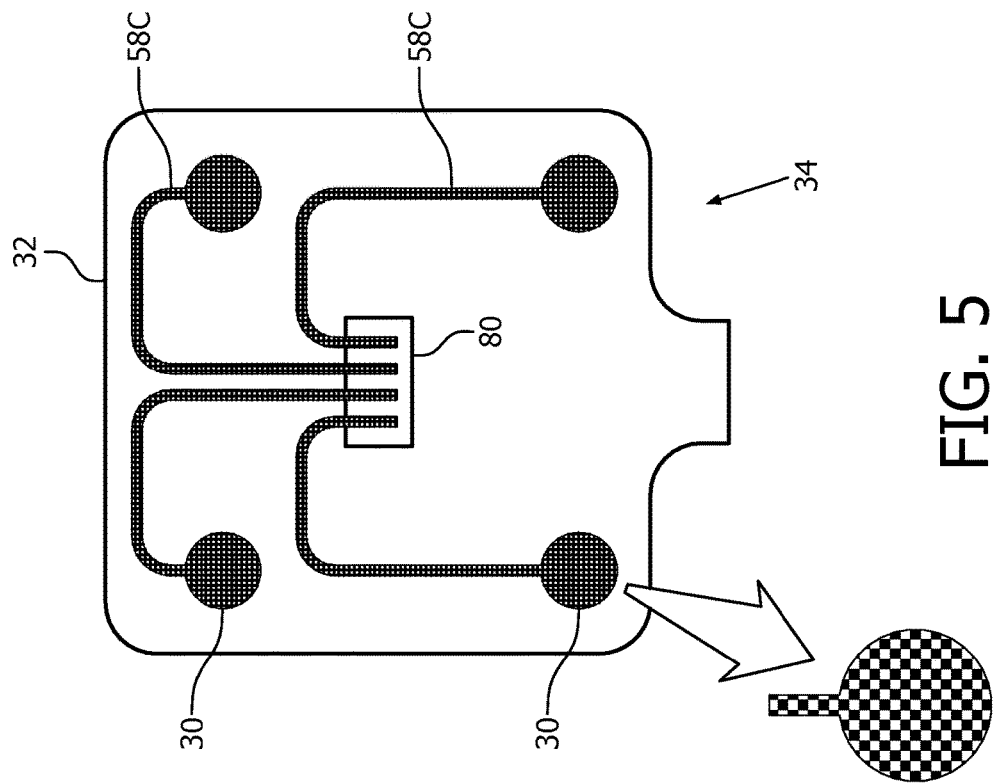

FIG. 5 diagrammatically shows an electrode patch with non-uniformly distributed high resistance printed circuitry.

Figure 6:
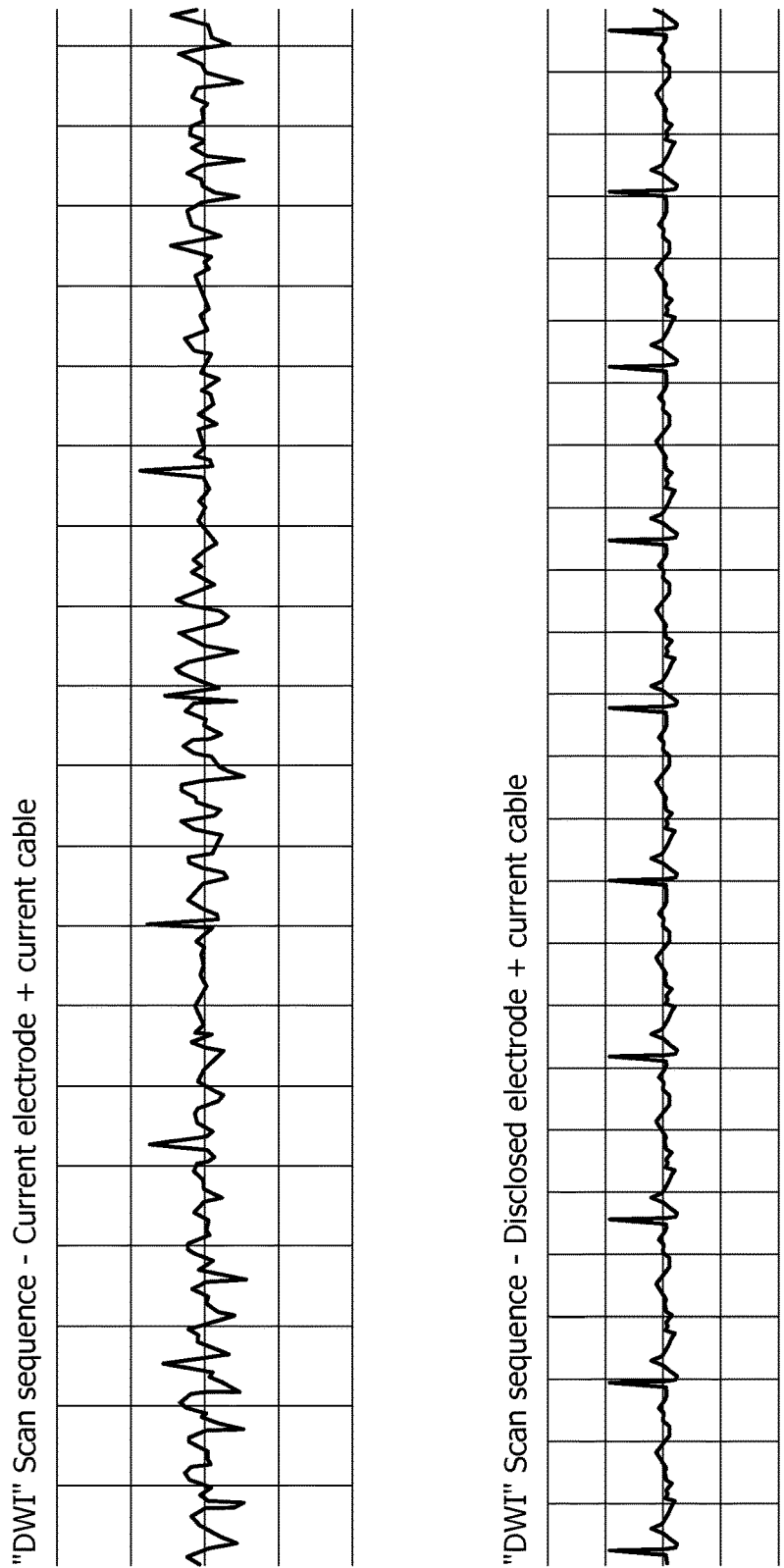
Figure 7:
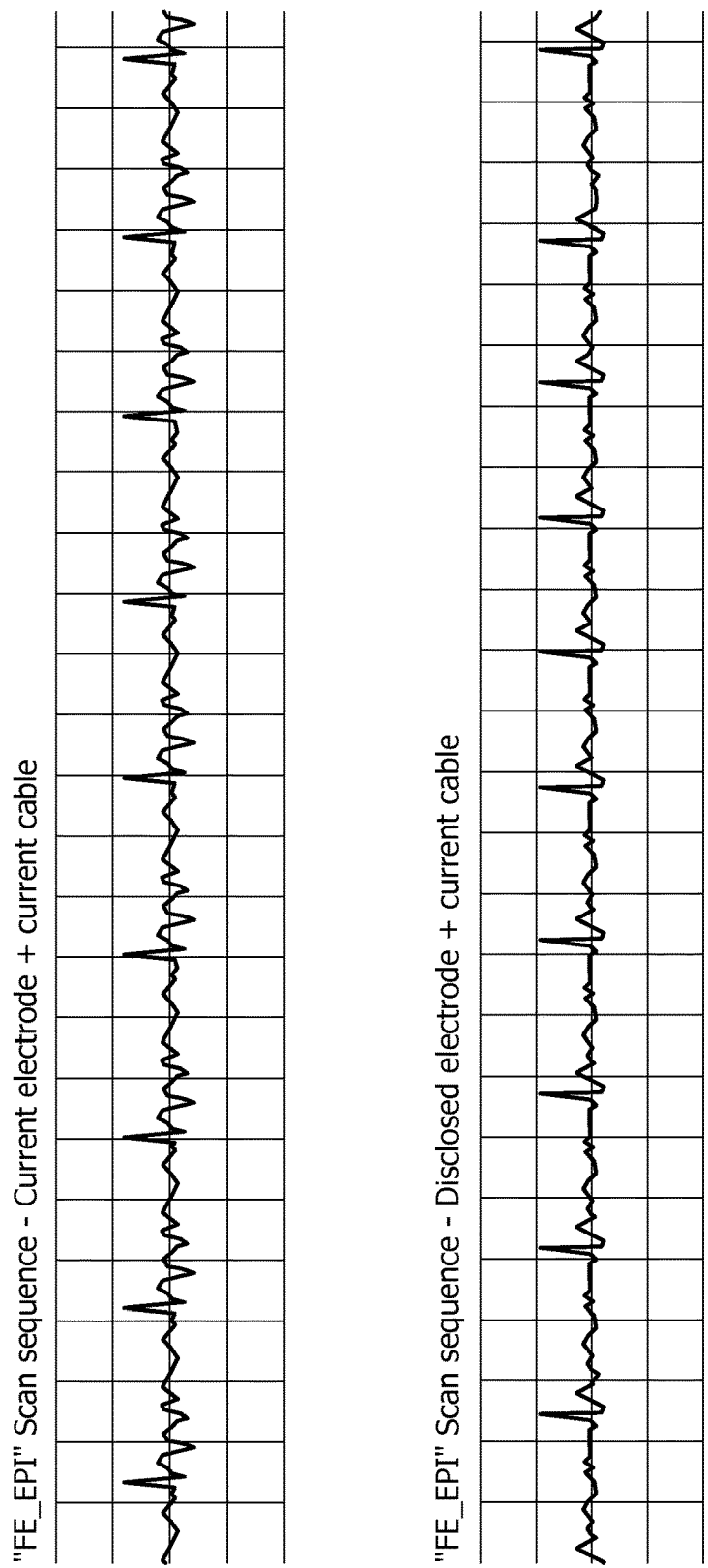
Figure 8:
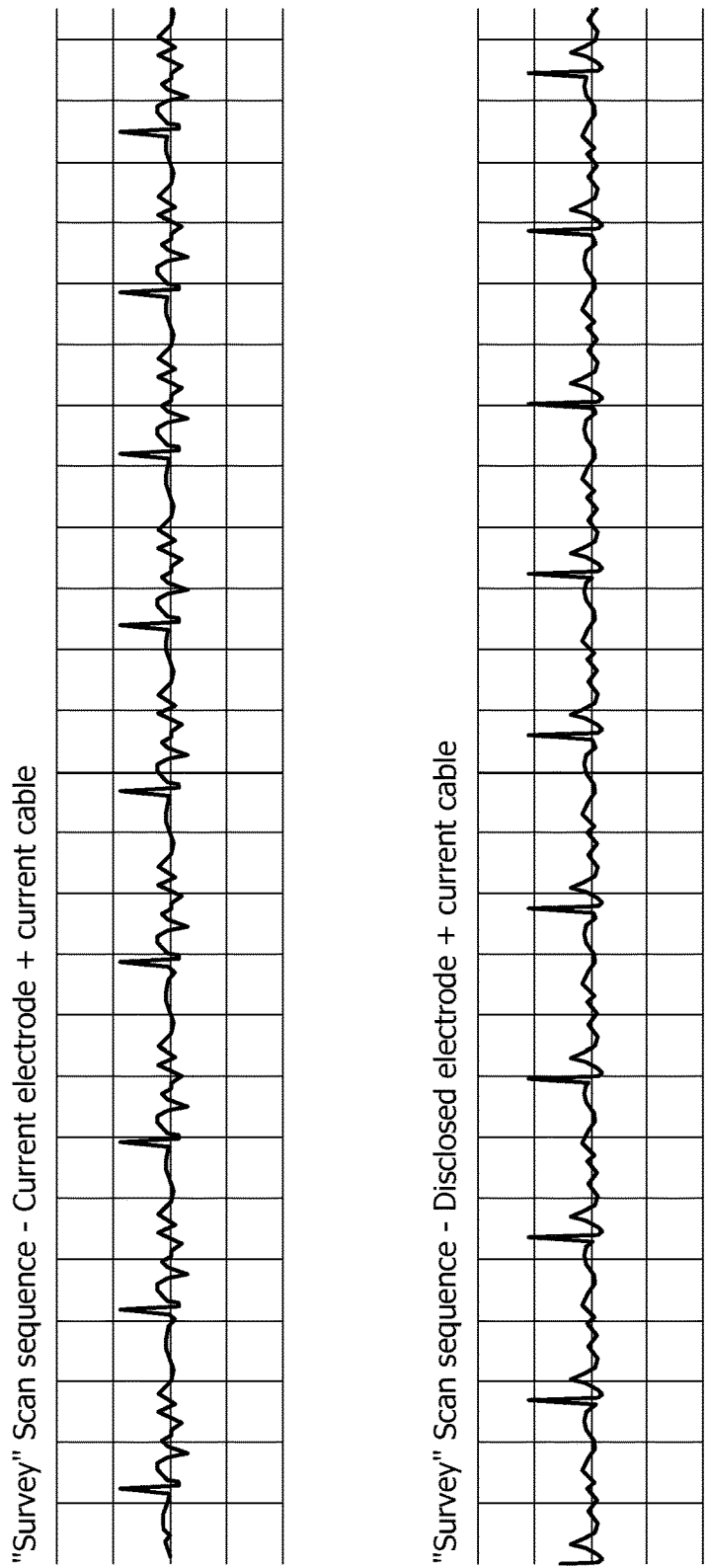

FIGS. 6-8 show ECG results acquired using conventional electrode patches with ECG results acquired using electrode patches as disclosed herein.

With reference to FIG. 1, a magnetic resonance environment includes a magnetic resonance (MR) scanner 10 disposed in a radio frequency isolation room 12 (diagrammatically indicated by a dashed box surrounding the MR scanner 10), for example, comprising a wire mesh or other radio frequency screening structures embedded in or disposed on the walls, ceiling, and floor of the MR room containing the MR scanner 10. The MR scanner 10 is shown in diagrammatic side-sectional view in FIG. 1, and includes a housing 14 containing a main magnet windings 16 (typically superconducting and contained in suitable cryogenic containment, not shown, although a resistive magnet windings are also contemplated) that generate a static ($B_0$) magnetic field in a bore 18 or other examination region. The housing 14 also contains magnetic field gradient coils 20 for superimposing magnetic field gradients on the static ($B_0$) magnetic field. Such gradients have numerous applications as is known in the art, such as spatially encoding magnetic resonance, spoiling magnetic resonance, and so forth. An imaging subject, such as an illustrative patient 22, or an animal (for veterinary imaging applications), or so forth is loaded into the examination region (inside the bore 18 in the illustrative case) via a suitable couch 24 or other patient support/transport apparatus. The MR scanner may include numerous additional components known in the art which are not shown for simplicity, such as optional steel shims, optional whole body radio frequency (RF) coil disposed in the housing 14, and so forth. The MR scanner also typically includes numerous auxiliary or ancillary components again not shown for simplicity, such as power supplies for the main magnet 16 and the magnetic field gradient coils 20, optional local RF coils (e.g. surface coils, a head coil or limb coil, or so forth), RF transmitter and RF reception hardware, and various control and image reconstruction systems, by way of some examples. Moreover, it is to be understood that the illustrative MR scanner 10, which is a horizontal-bore type scanner, is merely an illustrative example and that more generally the disclosed MR safe cables and electrodes are suitably employed in conjunction with any type of MR scanner (e.g., a vertical bore scanner, open-bore scanner, or so forth).

In operation, the main magnet 16 operates to generate a static $B_0$ magnetic field in the examination region 18. RF pulses are generated by the RF system (including for example a transmitter and one or more RF coils disposed in the bore or a whole-body RF coil in the housing 14) at the Larmor frequency (i.e., magnetic resonance frequency) for the species to be excited (usually protons, although other species may be excited, e.g. in MR spectroscopy or multi-nuclear MR imaging applications). These pulses excite nuclear magnetic resonance (NMR) in the target species (e.g., protons) in the subject 22 which are detected by a suitable RF detection system (e.g., a magnetic resonance coil or coils and suitable receiver electronics). Magnetic field gradients are optionally applied by the gradient coils 20 before or during excitation, during a delay period (e.g., time to echo or TE) period prior to readout, and/or during readout in order to spatially encode the NMR signals. An image reconstruction processor applies a suitable reconstruction algorithm comporting with the chosen spatial encoding in order to generate a magnetic resonance image which may then be displayed, rendered, fused or contrasted with other MR images and/or images from other modalities, or otherwise utilized.

With continuing reference to FIG. 1 and with further reference to FIG. 2, as part of the MR procedure, biopotential measurements are acquired using electrodes 30 disposed on an appropriate portion of the patient (e.g., on chest skin and optionally also on limb skin in the case of ECG, or on the scalp in the case of EEG, or so forth). In illustrative FIG. 1 four electrodes are disposed on a common substrate 32 to form an electrodes patch 34. The common substrate 32 provides defined spacing and a supporting substrate for the (illustrative four) electrodes. The number, arrangement, and location of electrodes are chosen for the particular application. In the case of ECG some common electrode configurations include EASI configurations and variants thereof, which typically include about five electrodes, and so-called 12-lead ECG which employs ten electrodes disposed on the chest and limbs in a standard 12-lead ECG configuration. In some embodiments the electrodes may be discrete, rather than being disposed on a common patch as in the illustrative example.

A cable 36 includes conductors in the form of electrically conductive traces 38 disposed on a substrate 40. Although electrically conductive, the traces 38 are highly resistive compared with conventional printed circuitry such as copper traces. For example, in some embodiments the traces 38 have sheet resistance $R_S$ of one ohm/sq or higher. (By comparison, a copper trace in typical printed circuitry has sheet resistance of about 0.05 ohm/sq or lower). More generally, the material resistivity ρ together with the thickness t and width W of the trace are chosen to provide the desired conductor resistance. As is known in the art, sheet resistance $R_S$ is given by the bulk resistivity ρ of the material forming the layer divided by the layer thickness t, i.e. $R_S=\rho/t$. Then the resistance R of a trace (i.e., conductor) of thickness t having length L and width W is given as $R=R_S \times (L/W)$.

In some embodiments the conductive traces 38 are formed from a mixture of conductive particles disposed in a solvent matrix, which is applied to the substrate 40. Upon curing the solvent dissipates leaving the conductive particles bonded to the substrate 40 by residue of the curing. In some embodiments the conductive traces 38 are formed of graphite, nanotubes, buckyballs, or other carbon-based particles disposed on the substrate 40 by screen printing or another deposition process to form the conductive traces 38. Instead of carbon-based particles, particles of other materials of suitable (bulk) resistivity and mechanical and thermal properties can be chosen, such as a doped semiconductor material, silicone particles, metal oxide materials, or so forth. Instead of screen printing, other processes can be used to form the traces 38 on the substrate 40, such as depositing a bulk layer and etching away to define the traces, depositing the traces by a vacuum evaporation process, or so forth. The material forming the traces 38 should also be non-ferromagnetic to avoid interference with the MR scanner.

The substrate 40 can be any substrate capable of supporting the conductors 38 in suitable electrical isolation. Some suitable substrates include a plastic or polymer substrate such as a Melinex® sheet or film (available from DuPont Teijin Films, Chester, Va.), a polyimide sheet or film, or so forth. The substrate should be electrically insulating as compared with the conductivity of the material of the traces 38; alternatively the substrate can be electrically conductive but including an electrically insulating layer on which the traces are disposed, where the electrically insulating layer is insulating as compared with the conductivity of the material of the traces 38. In some embodiments, the substrate 40 advantageously has some flexibility (as is the case for a Melinex® sheet or film) to enable the cable 36 to be somewhat flexible.

The cable 36 runs from the electrodes 30 to a receiver unit 42. In the illustrative example the receiver unit 42 is a wireless ECG module that receives the measured potential signals and transmits them via a wireless channel 44 (diagrammatically indicated in FIG. 1 by a dashed double-headed curved line) to an ECG monitor 46 located outside (or optionally inside) the MR room 12. The wireless ECG module 42 can be located inside the bore 18 (as illustrated) or outside (for example, by running the cable through a passageway through the MR housing 14 or out the open end of the bore 18). Moreover, it is contemplated to omit the wireless ECG module and instead run the cable directly to the ECG monitor (in which case the ECG monitor is the receiver unit), although this will generally require a substantially longer cable. The ECG monitor 46 is configured to process and display the acquired biopotential measurements. For example, in the illustrative case of the ECG monitor 46, the ECG data may be displayed as ECG traces, and may optionally be processed to detect R-wave occurrences or other ECG events for use in gating of the MR imaging or so forth. In some embodiments the acquired ECG (or other biopotential) data are stored on a non-transitory storage medium such as a hard disk drive, flash drive, or so forth, and/or are printed on paper (e.g., as ECG traces).

With reference to FIG. 3, a suitable configuration for the cable 34 and electrodes 30 is shown in side sectional view so as to show the conductor or trace 38 disposed on the substrate 40. Optionally, a protective layer 50 covers the traces 38 to provide electrical insulation and protection against damage by abrasion or the like. The protective layer 50 should be electrically insulating as compared with the material of the traces 38, and should be non-ferromagnetic and MR compatible. Some suitable embodiments of the protective layer 50 include a polymer or polymide sheet applied on top of the substrate 40 after depositing or otherwise forming the traces 38, or depositing an insulating plastic, polymer, or other material on top of the substrate 40 and traces 38 to form the protective layer 50. The protective layer 50 may also be a foam thermal insulating layer to provide patient comfort.

With continuing reference to FIG. 3, the electrode patch 34 can be formed similarly, with the common substrate 32 being a Melinex® sheet or film or other suitable substrate with appropriate electrically insulating and MR compatible properties, and with flexibility as desired. The common substrate 32 of the electrodes can be the same material as the substrate 40 of the cable 36 (as in illustrative FIG. 3), or can be different materials. The electrode 30 is disposed on a trace 58 formed on the substrate 32. The trace 58 can be of the same material and deposition technique as the traces 38 of the cable 36, e.g. a carbon-based printed trace. The traces 38 of the cable 36 and the traces 58 connecting and supporting the electrodes 30 can be of the same material (as illustrated), or can be different materials. The electrode 30 is formed on the trace 58 using a suitable layer or layer stack to facilitate electrical contact with skin 60 of the patient or other subject 22. In one suitable embodiment, the electrodes 30 include a silver layer 62 disposed on the carbon-based trace 58, and a silver chloride-based electrolyte layer 64 disposed on the silver layer 62. The electrolyte layer 64 can serve as an adhesive, or an additional adhesive layer can be provided (not shown). The electrode patch 34 preferably includes a protective layer 70 which may be the same material as the protective layer 50 of the cable 36. However, the protective layer 70 should include openings for the electrodes 30 to enable the electrodes 30 to contact the skin 60. It is contemplated to include a pull-off tab or other covering (not shown) disposed over the electrode 30 which is pulled off or otherwise removed just before the electrode is applied to the skin 60.

With continuing reference to FIG. 3, electrical connection between the electrode patch 34 and the cable 36 (or, between individual electrodes and the cable 36 in embodiments employing individual electrodes rather than a patch), and electrical connection between the cable 36 and the receiver unit 42 can take various forms. In the illustrative example of FIG. 3, at the end of the cable 36 distal from the electrodes patch 34 each conductor or trace 38 is coated with a layer or layer stack 72 of a suitably electrically conductive material (that is, more electrically conductive than the conductors or traces 38). In the illustrative example, layer 72 is a silver layer comparable to the silver layer 62 of the electrodes 30, but omitting the silver chloride coating 64. In other embodiments, the layer 72 may be silver, copper, or another material having higher conductivity than the material forming the trace 38. In some embodiments the layer 72 is an added piece of metal foil. The protective layer 50 does not cover these layers 72. The effect is to form an edge connector 74 that can plug into a mating socket of the receiver unit 42. Unless the distal end of the cable extends outside of the MR scanner, the layer or layers 72 should be made of an MR compatible material, e.g. a non-ferromagnetic material. Although not shown in FIG. 3, the connection between the electrodes patch 34 and the cable 36 can employ a similar arrangement except with a mating connector attached to one of the components 34, 36.

By manufacturing the cable 36 and the electrodes patch 34 as separate elements, the cable can be reused while the patch would typically be a disposable consumable item that is used once for a patient and then discarded. Alternatively, in some embodiments the electrodes patch 34 and the cable 36 are formed as a single unitary structure on a single-piece substrate that embodies both substrates 32, 40, and with the traces 38, 58 forming single continuous traces. This approach simplifies patient workflow as the single-piece ECG patch/cable is utilized by plugging the edge connector 74 into the mating socket of the receiver unit 42 (or alternatively into the mating socket of the ECG monitor), applying the electrodes 30 to the patient, and running the ECG. The step of connecting the cable with the ECG electrodes is eliminated. Because the cable and patch are fabricated as a single unitary structure, the additional cost of discarding the cable is reduced.

In various embodiments, the traces 38, 58 are suitably formed of carbon-based ink with specific electrical resistance applied to the planar flexible substrate 32, 40, such as polymer resin-based film, by any reproductive method, such as by screen printing. The printed trace 38, 58 may be solid or may contain features such as hatching to reduce eddy current generation in the trace or to vary resistance with identical geometry. The cable may have any number of conductors from 1 to 12 (or more, if appropriate for the application). For example, in a 12-lead ECG setup the cable may include 12 conductors 38, while in an EASI ECG setup only 5 conductors may be included. All conductors may be on a single substrate or may be on different substrates to accommodate various patient body shapes and/or to simplify cable routing.

In other contemplated aspects, the resistance of the conductors 38, 58 may be evenly or unevenly distributed along the trace 38, 58. Uneven distribution can be achieved, for example, by varying the trace width and/or thickness, or by using a "checkerboard" pattern or other nonuniform printing pattern for the trace. It is also contemplated to add electrical components to the cable 36 and/or to the electrode patch 34. For example, a discrete resistance component may be added, or a small region of higher-resistance material may be interposed along the trace to form a localized resistance. The cable 36 and/or electrode patch 34 is optionally surrounded by a protective shield (e.g., Faraday cage) to minimize electrical interference. Notch filters or low pass filters, integrated circuit components, antenna circuits, power supplies, sensors (e.g., piezo sensors or MEMS accelerometers), or optical elements are optionally be incorporated into the cable 36 and/or electrode patch 34 by adhering or otherwise attaching such components to the substrate 32, 40 and connecting to various traces 38, 58 as appropriate.

With reference to FIGS. 4 and 5, some illustrative configurations for the electrodes patch 34 are shown. In these embodiments, the patch 34 includes a connector 80 that may, for example, accept an edge connector (not shown) of the cable 36 that is similar to the edge connector 74 shown in FIG. 3, except located at the end of the cable 36 proximate to the electrodes patch 34. In the patch embodiment of FIG. 4, the traces 58 are continuous traces. In the patch embodiment of FIG. 5, traces 58C have the same layout as the traces 58, but are deposited in a "checkerboard" pattern with only 50% coverage (see inset of FIG. 5). By reducing the area coverage of the traces the sheet resistance $R_S$ is effectively increased (e.g., typically by a factor of about two for 50% area coverage).

By printing the electrode and lead connections, repeatability and reproducibility of the lead-wire routing is assured between cases and for the same patient. Patient movement is less likely to induce voltages or introduce noise to the biopotential measurement, because such motion does not change the relative spacing of the electrodes or the leads (i.e., conductors 38, 58). If the substrates 32, 40 have some flexibility then some motion related voltage induction and noise may result, but the amount of motion (and hence the introduced noise) is substantially reduced versus the case for individual wires. Moreover, a tradeoff between patient comfort and preparation convenience (facilitated by making the substrates flexible) and noise (suppressed by making the substrates rigid) can be achieved by appropriate design of the substrate flexibility (controlled, for example, by the thickness of the substrate, as a thicker substrate is generally less flexible).

The materials for the electrodes and the cable are selected so that proton emissions do not obscure the MR image, and to minimize contact impedance, and to minimize offset voltages. The disclosed cables and electrodes are readily constructed to be "MR Safe" rather than merely "MR Conditional". (The distinction is that for "MR safe" there should be no condition under which the component poses a risk to the patient or introduces functional limitations in the MRI).

Although in the disclosed embodiments the electrodes 30 are attached by adhesive, alternatively a mechanical mechanism can be used to attach the patch rather than adhesive. Moreover, materials other than silver-silver chloride may be used to create the electrode tissue interface circuit. For example, gel soaked sponge or paste may be used to create the electrode tissue interface circuit. As with protective layer 50, the protective layer 70 of the electrode patch 34 may advantageously be a foam thermal insulating layer.

With reference to FIGS. 6-8, test ECG results are shown for a prototype of the electrodes patch 34. The tests were performed in a Philips 3.0 T Achieva™ MRI Scanner. Several high dB/dT scan sequences were evaluated using an existing commercial electrode patch (i.e. "current electrode") versus the electrodes patch 34 (i.e., "Disclosed electrode"). Criteria used to evaluate performance include the R-wave to T-wave amplitude ratio (where the bigger the ratio, the better because it prevents the T-wave from being detected as an R-wave creating false triggering/synchronization to the MRI) and the variation (or RMS noise) in the baseline (where lower is the better because it prevents the R-wave from being obscured during R-wave detection). FIG. 6 shows results for a diffusion-weighted imaging (DWI) scan. FIG. 7 shows results for a field-echo, echo planar imaging (FE-EPI) scan. FIG. 8 shows results for a survey scan.

The invention has been described with reference to the preferred embodiments. Obviously, modifications and alterations will occur to others upon reading and understanding the preceding detailed description. It is intended that the invention be construed as including all such modifications and alterations insofar as they come within the scope of the appended claims or the equivalents thereof.

Having described the preferred embodiment, the invention is now claimed to be:

1. A device for use in biopotential measurements in a magnetic resonance (MR) environment, the device comprising:
   a cable including:
      a flexible plastic or polymer sheet extending as a single unitary structure from a first end to an opposite second end;
      an electrically conductive trace disposed on the flexible plastic or polymer sheet and running from the first end to the opposite second end, the electrically conductive trace having sheet resistance of one ohm/square or higher, the electrically conductive trace having a hatching or checkerboard pattern; and
   an electrode patch disposed on the electrically conductive trace at the second end, the electrode patch comprising a plurality of electrodes, the electrodes including:
      a layer of electrically conductive material disposed on the electrically conductive trace at the second end that is more electrically conductive than the material comprising the electrically conductive trace, and
      an attachment layer disposed on the layer of electrically conductive material and configured to attach the electrode to human skin, the attachment layer comprising silver chloride;
   wherein the cable and the electrode patch are attachable and detachable to each other via a mating connector disposed on one of the cable and the electrode patch.

2. The device of claim 1, wherein the layer of electrically conductive material of the electrode comprises a silver layer.

3. The device of claim 1, wherein the attachment layer is adapted to adhere to human skin to effect attachment of the electrode to human skin.

4. The device of claim 1, further comprising:
   a connector disposed at the first end and configured to connect with a monitor or receiver unit, the electrically conductive trace conducting biopotential measurements from the electrode to the connector.

5. The device of claim 1, wherein the electrically conductive trace is an electrically conductive carbon trace.

6. The device of claim 1, further comprising:
   an electrically insulating protective layer disposed on the flexible plastic or polymer sheet and covering the electrically conductive trace but not the electrode, the electrically insulating protective layer including a plurality of openings.

7. A biopotential measurement apparatus comprising:
   a monitor or receiver unit configured to receive biopotential measurements; and
   a device as set forth in claim 1 connecting the electrode patch with the monitor or receiver unit.

8. The biopotential measurement apparatus of claim 7, wherein the monitor or receiver unit is an electrocardiography (ECG) instrument.

9. A device for use in biopotential measurements in a magnetic resonance (MR) environment, the device comprising:
   a cable, including:
      a flexible plastic or polymer sheet extending as a single unitary structure from a first end to an opposite second end;
      an electrically conductive trace formed by vacuum evaporation or screen printing on the flexible plastic or polymer sheet and running from the first end to the opposite second end, the electrically conductive trace having sheet resistance of one ohm/square or higher, the electrically conductive trace having a hatching or checkerboard pattern;
      an electrically insulating protective layer disposed on the flexible plastic or polymer sheet and covering the electrically conductive trace; and
      an edge connector at the first end comprising a layer or layer stack of electrically conductive material disposed on the electrically conductive trace at the first end that is more electrically conductive than the material comprising the electrically conductive trace, the electrically insulating protective layer not covering the layer or layer stack of electrically conductive material; and
   an electrode disposed on the electrically conductive trace at the second end, the electrode configured for attachment to human skin, the electrically conductive trace electrically connecting the edge connector and the electrode, the electrically insulating protective layer not covering the electrode.

10. The device of claim 9, wherein the material comprising the electrically conductive trace includes carbon and the layer or layer stack of electrically conductive material includes a silver layer.

11. The device of claim 9, wherein the material comprising the electrically conductive trace is a metal oxide.

12. The device of claim 9, wherein the material comprising the electrically conductive trace is a doped semiconductor.

13. The device of claim 9, wherein the electrode comprises a layer of electrically conductive material disposed on the electrically conductive trace at the second end that is more electrically conductive than the material comprising the electrically conductive trace.

14. The device of claim 9, wherein the electrode comprises:
   a silver layer disposed on the electrically conductive trace at the second end; and
   a silver chloride-based electrolyte layer disposed on the silver layer.

15. A device for use in biopotential measurements in a magnetic resonance (MR) environment, the device comprising:
   a cable, including:
      a flexible plastic or polymer sheet extending as a single unitary structure from a first end to an opposite second end;
      an electrically insulating protective layer disposed on the flexible plastic or polymer sheet and covering the electrically conductive trace and
      an electrically conductive trace formed by vacuum evaporation or screen printing on the flexible plastic or polymer sheet and running from the first end to the opposite second end, the electrically conductive trace having sheet resistance of one ohm/square or higher, the electrically conductive trace having a hatching or checkerboard pattern.

16. The device of claim 15, further comprising:
   an electrode disposed on the electrically conductive trace at the second end, the electrode configured for attachment to human skin.

* * * * *